(12) United States Patent
Hannibal

(10) Patent No.: US 11,384,113 B2
(45) Date of Patent: Jul. 12, 2022

(54) COBALAMIN DERIVATIVES AND THEIR USE FOR THE TREATMENT OF DISEASES CAUSED BY LACK OF VITAMIN B12 SUPPLY

(71) Applicant: Albert-Ludwigs-Universitaet Freiburg, Freiburg (DE)

(72) Inventor: Luciana Hannibal, Voerstetten (DE)

(73) Assignee: Albert-Ludwigs-Universitaet-Freiburg, Freiburg (DE)

( * ) Notice: Subject to any disclaimer, the term of this patent is extended or adjusted under 35 U.S.C. 154(b) by 25 days.

(21) Appl. No.: 16/615,014

(22) PCT Filed: May 24, 2018

(86) PCT No.: PCT/EP2018/063597
§ 371 (c)(1),
(2) Date: Nov. 19, 2019

(87) PCT Pub. No.: WO2018/215578
PCT Pub. Date: Nov. 29, 2018

(65) Prior Publication Data
US 2020/0079816 A1    Mar. 12, 2020

(30) Foreign Application Priority Data
May 24, 2017    (EP) .................................... 17172613

(51) Int. Cl.
*C07H 23/00*       (2006.01)
*A23L 33/15*       (2016.01)
(52) U.S. Cl.
CPC .............. *C07H 23/00* (2013.01); *A23L 33/15* (2016.08); *A23V 2002/00* (2013.01)
(58) Field of Classification Search
CPC ...... C07H 23/00; A23L 33/15; A23V 2002/00
USPC ......................................................... 514/52
See application file for complete search history.

(56) References Cited

FOREIGN PATENT DOCUMENTS

WO    WO 02/087593    11/2002

OTHER PUBLICATIONS

Dauncey (Nutrients 2013, 5, 887-914).*
Adler et al. (Journal of the American Chemical Society / 88:21 / Nov. 5, 1966).*
Kitagawa et al. (Bull. Chem. Soc. Jpn., 64, 2942-2947 (1991)).*
D. Dolphin et al., *J. Chem. Soc.*, pp. 2174-2181 (Jan. 1, 1965).
J. Grate et al., *J. Am. Chem. Soc.*, pp. 1588-1594 (Mar. 1, 1982).
R. Mukherjee et al., *Inorganic Chemistry*, vol. 48, No. 19, pp. 9526-9534 (Oct. 5, 2009).
F. Nome et al., *J. Chem. Soc.*, vol. 13, pp. 1212-1219 (Jan. 1, 1976).

(Continued)

*Primary Examiner* — Shaojia A Jiang
*Assistant Examiner* — Michael C Henry
(74) *Attorney, Agent, or Firm* — Smith Patent, LLC; Chalin A. Smith

(57)    ABSTRACT

The present invention concerns cobalamin derivatives of formula (I)

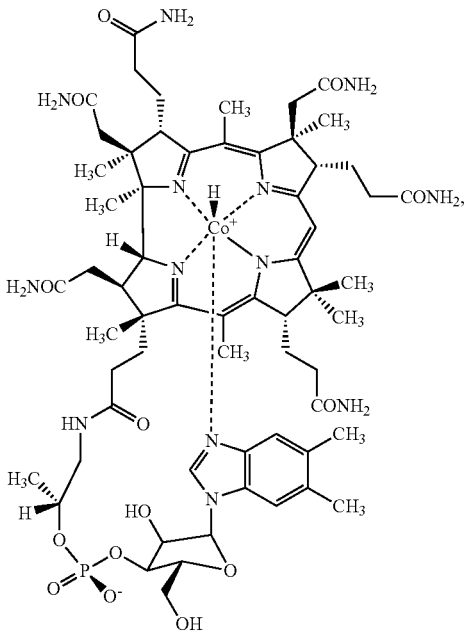

wherein X is a ligand having a formula selected from among:
—(CH$_2$)$_{1-5}$—S—(CH$_2$)$_{0-3}$—CH$_3$,    —S—(CH$_2$)$_{1-5}$—NH$_2$
and

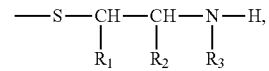

further wherein R$_1$ is H, methyl or ethyl, R$_2$ is

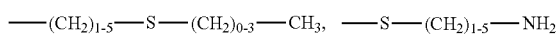

and R$_3$ is —H or

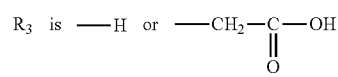

and its use in diseases caused by lack of vitamin B$_{12}$ support.

11 Claims, 12 Drawing Sheets

(56) References Cited

OTHER PUBLICATIONS

E. Scheuring et al., *Biochemistry*, vol. 33, No. 20, pp. 6310-6315 (May 1, 1994).

J.E. Dominy et al., "Discovery and characterization of a second mammalian thiol dioxygenase, cysteamine dioxygenase", *J Biol Chem*. (2007), 282(35):25189-98.

L. Gallego-Villar et al., "Cysteamine Revisited: Repair of Arginine to Cysteine Mutations", *J. Inherit. Metab. Dis.* (2017), 40: 555-567.

L. Hannibal et al., "Processing of Alkylcobalamins in Mammalian Cells: A Role for the MMACHC (Cblc) Gene Product", *Mol Genet Metab* (2009), 97(4): 260-266.

J. Kim et al., "Decyanation of Vitamin B12 by a Trafficking Chaperone", *PNAS USA* (2008), 105(38): 14551-14554.

J. Kim et al., A Human Vitamin B12 Trafficking Protein Uses Glutathione Transferase Activity for Processing Alkylcobalamins. *J Biol Chem*. (Nov. 2009), 284(48): 33418-33424.

M. Ruetz et al., "Access to Organometallic Arylcobaltcorrins Through Radical Synthesis: 4-Ethylphenylcobalamin, A Potential Antivitamin B(12)", *Angew Chem Int Ed Engl*. (2013), 52(9):2606-10.

E. Suarez-Moreira et al., "A Simple, Convenient Method to Synthesize Cobalamins: Synthesis of Homocysteinylcobalamin, N-Acetylcysteinylcobalamin, 2-N-Acetylamino-2-Carbomethoxyethanethiolatocobalamin, Sulfitocobalamin and Nitrocobalamin", *Dalton. Trans.* (2006), pp. 5269-5277.

R.K. Suto, et al., "Synthesis, Characterization, Solution Stability, and X-ray Crystal Structure of the Thiolatocobalamin γ-Glutamylcysteinylcobalamin, a Dipeptide Analogue of Glutathionylcobalamin: Insights into the Enhanced Co—S Bond Stability of the Natural Product Glutathionylcobalamin", *Inorganic Chemistry* (2001), 40(12): 2686-2692.

V. Wingert, et al., "Thiolatocobalamins Repair the Activity of Pathogenic Variants of the Human Cobalamin Processing Enzyme CblC". *Biochimie* (2021), 183: 108-125.

* cited by examiner 5 a 5 b 5 c

CyaCbl

MPGCbl

COBALAMIN DERIVATIVES AND THEIR USE FOR THE TREATMENT OF DISEASES CAUSED BY LACK OF VITAMIN B12 SUPPLY

PRIORITY

This application corresponds to the U.S. National phase of International Application No. PCT/EP2018/063597, filed May 24, 2018, which, in turn, claims priority to European Patent Application No. 17.172613.6 filed May 24, 2017, the contents of which are incorporated by reference herein in their entirety.

BACKGROUND

Mammals utilize $B_{12}$ or cobalamin derivatives as cofactors for two enzymes, namely methionine synthase and methylmalonyl-CoA mutase. Methionine synthase catalyzes the methylation of homocysteine to form the amino acid methionine concomitantly with the regeneration of tetrahydrofolate from 5-methyltetrahydrofolate. This reaction is strictly dependent on methylcobalamin (MeCbl). Tetrahydrofolate is required to support the biosynthesis of purines and pyrimidines and therefore it is essential for cellular proliferation and homeostasis. Methylmalonyl-CoA mutase is a clearing-house for methylmalonyl-CoA generated during breakdown of cholesterol, branched-chain amino acids and odd-chain fatty acids, and it converts methylmalonyl-CoA to succinyl-CoA, which supports energy metabolism. The reaction of methylmalonyl-CoA mutase is strictly dependent on 5'-deoxyadenosylcobalamin (AdoCbl). Since mammals lack the ability to synthesize cobalamins de novo they evolved strategies to assimilate dietary $B_{12}$ in the two biologically active cofactor forms, MeCbl and AdoCbl.

For a sufficient supply of cobalamin in the cells of a mammal the cobalamin must be first transported from the food to the body cells and second the mammalian organism must be able to use the cobalamin by a proper intracellular processing pathway, which is strictly dependent on the activity of the CblC enzyme (also known as MMACHC, $B_{12}$ chaperone, and CblC chaperone). The absorption of $B_{12}$ and its subsequent distribution in the body is mediated by a complex set of carrier proteins, receptors and transporters and it is possible to describe a coherent pathway of $B_{12}$ from food to the body cells. The transport of $B_{12}$ in extracellular fluids is dependent on three homologous carrier proteins, namely intrinsic factor, transcobalamin (also known as transcobalamin II) and haptocorrin (also known as the R-protein or transcobalamin I). A failure in the gastrointestinal uptake pathway is the most common cause of non-dietary-induced $B_{12}$ deficiency diseases (Nielsen et al., Nature Reviews (2012), 345-354).

It has been reported that in elderly people, a latent vitamin $B_{12}$ deficiency may be associated with progressive brain atrophy. Moderately elevated concentrations of homocysteine have been associated with an increased risk of dementia, notably Alzheimer's disease. The causes of vitamin $B_{12}$ deficiency may have several different reasons. One reason may be caused by insufficient dietary intake of vitamin $B_{12}$ whereby the high-risk groups include vegetarians, vegans and older people. Another reason may be a malabsorption of vitamin $B_{12}$ due to a lack of intrinsic factor of parietal cells, a disturbed uptake of vitamin $B_{12}$ from food due to gastric acid deficiencies or due to drug interactions. Other reasons may be found in intestinal diseases like e.g. intestinal resection, tropical sprue or Crohn's disease.

With regard to the processing of vitamin $B_{12}$ in the cells there are cobalamin disorders which are rare and inherited in an autosomal recessive manner. Cobalamin disorders are classified into several distinct complementation groups. Usually mutations cause a defect in the biochemical pathway that lead to the biosynthesis of MeCbl and AdoCbl, and the diseases are manifested as homocystinuria and methylmalonic aciduria. CblC processes cobalamins entering a cell to a common intermediate, cob(II)alamin/cob(I)alamin. Mutations in CblC represent the most common inborn error of cobalamin metabolism (Gherasim et al., The Journal of Biological Chemistry, vol. 290 (2015) pp 11393-11402).

SUMMARY OF THE INVENTION

It is an object of the present invention to provide sulfur-containing cobalamin derivatives which are helpful in the treatment of vitamin $B_{12}$-related defects caused either by a reduced uptake of vitamin $B_{12}$ from the food to the cells in need thereof or by a genetic defect or other interference in the pathway for transport and intracellular processing of $B_{12}$. Such cobalamin derivatives have in particular improved bioactivity.

The use of the sulfur-containing cobalamin derivatives described in this invention is related to vitamin $B_{12}$ deficiencies that a brought about by: 1) patients with inherited metabolic diseases that impair transport and intracellular cobalamin utilization; 2) individuals exposed to low vitamin $B_{12}$ intake (extreme poverty and strict vegetarians/vegans); 3) the elderly. Subjects in these categories may benefit by enhancement of the intracellular CblC—cobalamin processing machinery and its downstream enzymatic reactions.

Patients having a genetic defect of cobalamin metabolism belonging to the CblC group exhibit impairments in methionine synthase and methylmalonyl-CoA mutase which is consistent with the gene product MMACHC (for methylmalonic aciduria type C and homocystinuria). It has been suggested to rename this protein as cyanocobalamin decyanase (Kim et al., PNAS (2008) pp 14551-14554). Hannibal et al. (Molecular Genetics and Metabolism (2009) pp 260-266) reported that cell lines derived from patients having a mutated cblC protein did not process alkylcobalamin to the same extent as normal skin fibroblast cell lines.

The compounds described in this invention are sulfur-containing cobalamins, featuring either Co—S or Co—C axial bonds that act by enhancement of normal CblC enzymatic activity, by repairing a pathogenic variant of the CblC protein, or by replacing an absent CblC protein.

Vitamin $B_{12}$ derivatives, also referred to as cobalamins, play an important role in $B_{12}$ enzymes. The cobalamin structure is a coordination complex with six coordination sites binding a $Co^{3+}$ ion which is ligated equatorially by four nitrogens from the tetrapyrrole corrin ring and axially by ligands in an upper β-position and a lower α-position. The α-position ligand is coordinated to Co from the nitrogen atom of the nucleotide base, 5,6-dimethylbenzimidazol (DMB), which is connected to the corrin ring by a nucleotide structure. The complex can exist in three oxidation states of cobalt, namely Co(III), Co(II) and Co(I). The cobalamin has the formula (I) which is shown below.

In formula (I) possible ligands that can bind in the β-position are represented by "X". Important β-ligands are cyanide ($CN^-$) in cyanocobalamin (CNCbl(III)), water ($H_2O$) in aquocobalamin ($H_2$OCbl(III)), alkyl groups such as $CH_3$— in methylcobalamin (MeCbl(III)) and 5-deoxyadenosyl in adenosylcobalamin (AdoCbl(III)) which are cofactors for $B_{12}$-dependent human enzymes.

The present invention provides sulfur-containing cobalamin derivatives that have the formula of vitamin $B_{12}$ whereby, however, the ligand X has a different meaning. Such cobalamins are helpful since they have an improved efficacy in the treatment of various vitamin $B_{12}$ deficiencies. The present invention provides cobalamin derivative of formula (I)

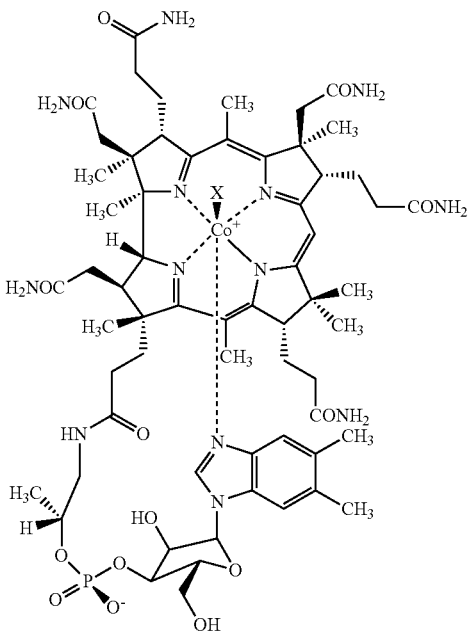

wherein X is a ligand having a formula selected from the group consisting of:

—(CH$_2$)$_{1-5}$—S—(CH$_2$)$_{0-3}$—CH$_3$,

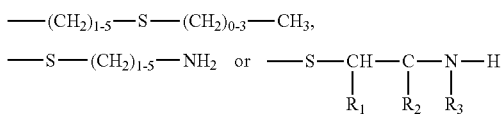

wherein R$_1$=H, methyl or ethyl,

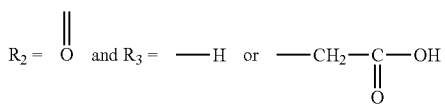

In particular preferred embodiments the cobalamin of formula (I), has a ligand X which is

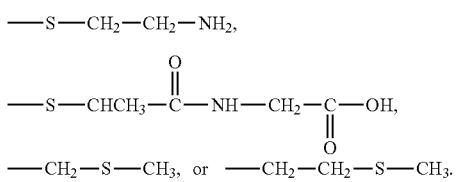

The cobalamin derivatives of the present invention can be used for the treatment of diseases related with a reduced vitamin $B_{12}$ support. These diseases may be caused by rare genetic defects of the cblC gene, which show homocystinuria and methylmalonic aciduria or other impairments of the proper utilization of vitamin $B_{12}$ in the cells. Alternatively, the cobalamin derivatives may be used for the treatment of elderly patients who do not have sufficient support of vitamin $B_{12}$. Such persons show frequently signs of mental impairment such as dementia or Alzheimer's disease.

The cobalamin derivatives of the present invention can be applied in an orally applicable formulation whereby the pharmaceutical formulations are preferably prepared to liberate the pharmaceutically active ingredient in the small intestine and the colon. Preferred are tablets or capsules that have an acid-resistant coating. After the tablet or capsule has passed the stomach, the coating is dissolved in the intestine due to a change of the pH value and the active ingredient is liberated in the small intestine in high concentration. This can be achieved by a coating with one or more film layers, which dissolve depending on the pH. Preferably such coatings are Eudragit® polymers which are acid resistant and dissolve at a pH of about 5.8 to 7.0.

Alternatively the cobalamin derivative can be applied as a parenterally applicable formulation like an injection solution. Since the cobalamin derivatives of the present invention may be easily degraded by the action of light it is preferred to provide the injection solution in a lyophilized form which can be reconstituted by the addition of sterile water or buffer immediately before application. The containers of the lyophilized cobalamin derivative should be protected from light.

In an alternative embodiment the cobalamin derivatives of the present invention can be provided as a food supplement. The food supplement may contain the cobalamins in the form of particles, which contain also additives like carriers or matrix builders. Preferred examples are starch, carrageenan, guar or sugars like lactose, fructose or saccharose.

In a further embodiment the present invention provides a process for the preparation of a cobalamin derivative of formula (I)

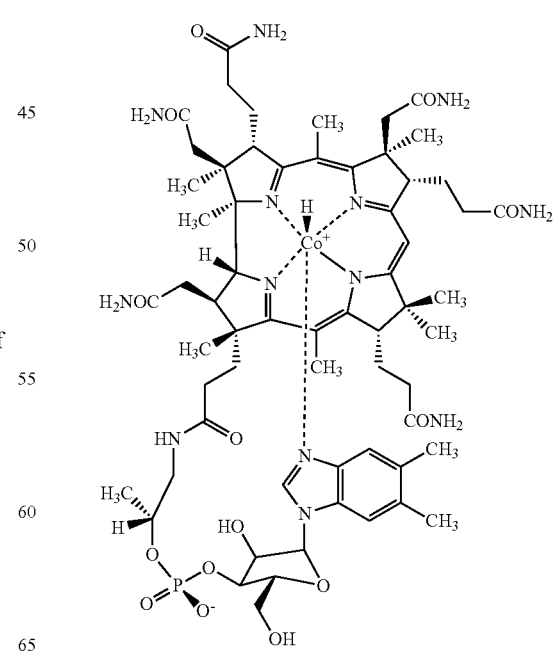

wherein the ligand X has the meaning

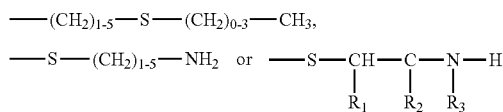

whereby $R_1$=H, methyl or ethyl,

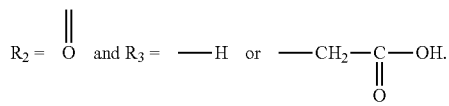

As starting material preferably commercially available cobalamins like hydroxycobalamin hydrochloride is used. The hydroxycobalamin hydrochloride is reacted with the ligand structures having a thiol group like for example cysteamine or mercaptopropionylglycine or a reactive C containing group like for example chloro-methyl-methylsulfide or 1-chloro-2-methylsulfanyl. All syntheses are preferably carried out under red-light-only conditions due to the potential light sensitivity of both thiolatocobalamins and alkylcobalamins. Usually the syntheses were carried out under aerobic conditions.

The cobalamin derivatives of the present invention have the advantage of an improved bioactivity. Therefore, the cobalamin derivatives can be used for the treatment of diseases which are related to a decreased support or a decreased processing of the cobalamin in the cellular processing steps. The cobalamin derivatives of the present invention can be used for the treatment of inherited diseases, which affect the CblC protein. The diseases may also be caused by a reduced uptake of vitamin $B_{12}$.

In a further embodiment the cobalamin derivatives of the present invention can be used for the treatment of vitamin $B_{12}$ deficiency which expresses itself by a wide variety of neurological manifestations, such as paraesthesias, skin numbness, coordination disorders and reduced nerve conduction velocity. In elderly people, a latent vitamin $B_{12}$ deficiency can be associated with a progressive brain atrophy. It has been observed that raised plasma concentrations of homocysteine are associated with regional and whole brain atrophy, not only in Alzheimer's disease but also in healthy elderly people.

For the treatment of cognitive impairment, the choice between oral or parenteral administration is important. It is understood that parenteral administration of vitamin $B_{12}$ is ineffective since in particular with elderly people the malabsorption, frequently intestinal diseases or disorders affecting the utilization of vitamin $B_{12}$ play an important role. Therefore, parenteral administration might be required. However, parenteral administration is more difficult than oral administration since medically trained people like doctors or nurses are required. An advantage of the cobalamins of the present invention, namely an improved bioactivity and bioavailability, allows the application of the cobalamin derivatives in orally applicable formulations.

The cobalamin derivatives of the present invention can be used in elderly persons with a decline in cognitive performance. Furthermore, it can be used for the treatment of depression, which is in the elderly frequently associated with a low vitamin $B_{12}$ status and increased homocysteine and methylmalonic acid levels. The cobalamin derivatives of the present invention can also be used to treat or avoid the risk of Alzheimer's disease since raised homocysteine levels are associated with the risk of Alzheimer's disease. Therefore, the cobalamin derivatives of the present invention can be used not only for the treatment but also for the prophylaxis of dementia or Alzheimer's disease.

The sulfur-containing cobalamin compounds of the present invention refer to Co—S and Co—C bonded cobalamins exhibiting the following properties which are superior compared to current therapeutic forms of hydroxycobalamin (HOCbl) and cyanocobalamin (CNCbl) and methylcobalamin (MeCbl) as used in certain countries like Japan, namely:
a higher pKa of the base-on to base-off transition;
a higher redox potential for the reduction of the cobalt center and
more facile removal of the β-axial ligand.

Further, the cobalamin compounds described in the present application have the following advantages with respect to the thiolatocobalamin glutathionylcobalamin (GSCbl):
Superior repair of the enzymatic activity of pathogenic variants of the cobalamin processing enzyme CblC
Longer-lasting reduction of toxic MMA in cblC human fibroblasts

DETAILED DESCRIPTION OF THE INVENTION

In the following description the used abbreviations have the following meaning:

| | |
|---|---|
| Cbl | Cobalamin |
| Vitamin $B_{12}$, $B_{12}$ | Generic term for the vitamin, regardless of the chemistry of the beta-axial ligand |
| Cbi | Cobinamide |
| EPPS | 4-(2-Hydroxyethyl)-1-piperazinepropanesulfonic acid |
| Cya | Cysteamine |
| MPG | Mercaptopropionylglycine |
| $k_{obs}$ ($s^{-1}$) | Observed reaction rate |
| K ($M^{-1} s^{-1}$) | Concentration-dependent reaction rate |
| MeCbl | Methylcobalamin |
| AdoCbl | Adenosylcobalamin |
| HOCbl | Hydroxocobalamin |
| $H_2OCbl^+$ | Aquacobalamin |
| Co—S | Cobalt-sulfur bond |
| Co—C | Cobalt-carbon bond |
| Thiolatocobalamin | Cobalamin derivatives having Co—S axial ligation |
| Alkylcobalamin | Cobalamin derivatives having Co—C axial ligation |
| Processing of cobalamins | A reaction catalyzed by the CblC protein, to remove the beta-axial ligands of cobalamins with reduction of their cobalt center, under a base-off configuration |
| Cob(III)alamin | Fully oxidized form of cobalamin (such as in the case of MeCbl, AdoCbl, CNCbl, HOCbl, GSCbl, CyaCbl, MPGCbl) |
| Cob(II)alamin | One-electron reduced form of cobalamin |
| Cob(I)alamin | Two-electron reduced form of cobalamin |
| CblC protein | Cyanocobalamin decyanase |
| NHE | Normal Hydrogen Electron |
| MPGCbl | Mercaptopropionylglycine derivative of cobalamin, a thiolatocobalamin |
| CyaCbl | Cysteamine derivative of cobalamin, a thiolatocobalamin |

The present invention concerns the synthesis of new sulfur-containing cobalamin derivatives featuring Co—S or Co—$C_n$—S—R axial coordination, with: (a) increased pKa of the base-on to base-off configuration, (b) higher midpoint potential, and (c) facile removal of the p-axial ligand.

Certain p-axial ligands in this invention are selected and synthesized to provide bonding interactions that will compensate for the loss of function of abnormal variants of the CblC protein, due to naturally occurring mutations that lead to disease. The functional groups in the preferred cysteamine and mercaptopropionylglycine moieties provide opportunities for additional hydrogen-bond formation (compared to current therapeutic forms HOCbl or CNCbl) with amino acid residues in the cobalamin binding site of the CblC protein, which could be critical for restoring binding and enzymatic activity in pathogenic variants of CblC. Likewise, sulfur-containing Co—C-ligated cobalamins in this invention are analogues of the natural cofactor methylcobalamin, shown to be the preferred Co—C substrate by the indispensable cobalamin processing enzyme CblC.

Equilibrium of Base-on to Base-Off Configuration

Figure 1:
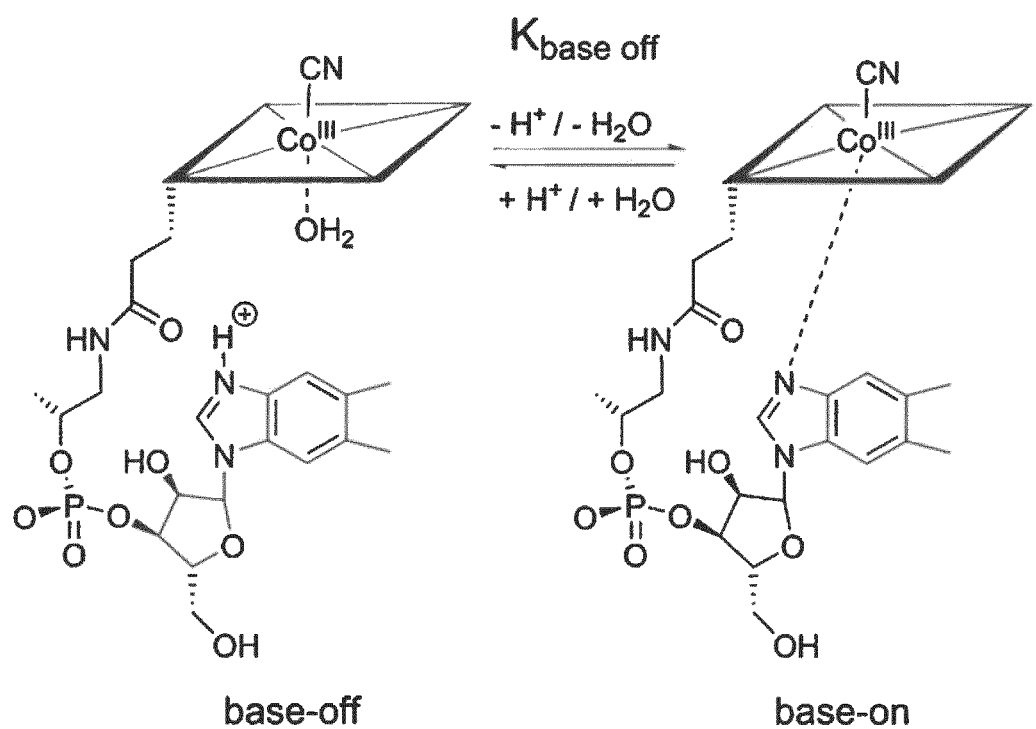
FIG. 1 shows the structure of cyanocobalamin (therapeutic form available in oral supplements and also in injections) in its base-on and base-off configurations.

At physiological pH, all cobalamins exist in the base-on configuration, where the α-axial ligand dimethylbenzimidazole is coordinated to the cobalt center via a nitrogen atom. A scheme of the base-on to base-off transition of cobalamins is provided in FIG. 1. The pKa for this transition is 0.10. This pH is unattainable under physiological conditions. This transition requires very acidic pHs, which are not within the reach of the cellular milieu. Table 1 shows pKa values for several β-ligands.

TABLE 1 pKa for the base-on to base-off equilibrium of selected cobalamins

| Upper axial ligand | pKa of base on/base off |
|---|---|
| $H_2O$ | −2.40 |
| $NO_2$ | −0.15 |
| $CN^-$ | 0.10 |
| Me | 2.90 |

TABLE 1-continued pKa for the base-on to base-off equilibrium of selected cobalamins

| Upper axial ligand | pKa of base on/base off |
|---|---|
| $SCN^-$ | 3.40 |
| Ado | 3.50 |
| formyl- | 3.70 |
| EtPh | 3.70 |
| acetyl- | 3.90 |
| propionyl- | 4.00 |
| $SO_2^{\sigma-}$ | 4.80 |
| NO | 5.10 |

As can be seen from Table 1, the nature of the p-axial ligand has a profound impact on the pKa of the base-on to base-off equilibrium. This property is relevant for the present invention since the new cobalamin derivatives featuring higher pKa of base-on to base-off transition increase their bioactivity. This increased bioactivity refers to greater ability of wild type and pathogenic variants of the processing enzyme CblC of utilizing new cobalamins as substrates to generate activated intermediates that are delivered to the acceptor cobalamin-dependent enzymes methionine synthase and methylmalonyl-CoA mutase.

Redox Potential for the Formation of Cellular Bioactive Cob(11)Alamin and Cob(1)Alamin An additional aspect of Cbl chemistry relevant to their behavior in biological systems concerns the midpoint potential for the reduction of the cobalt center, which is essential for the subsequent processing (removal of the β-axial ligand) via reductive mechanisms, including nucleophilic attack by reduced glutathione (GSH). Table 2 shows a summary of the midpoint redox potential for biologically active Cbls.

TABLE 2

Redox potentials for selected cobalamins or cobinamide (Cbi)

| Redox pair | Redox potential [V] relative to NHE | |
|---|---|---|
| electrochemical MeCbl(III) | −1.20 | 20° C. |
| electrochemical AdoCbl(III) | −1.04 | DMF/methanol |
| electrochemical CNCbl(III) | −0.76 | DMSO/propanol |
| Cbl(II) base-on/Cbl(I) | −0.61 | 22° C. |
| Cbl(II) base-off/Cbl(I) | −0.50 | |
| $H_2OCbl(III)$ base-on/Cbl(II) | 0.20 | 22° C. |
| base-on $(H_2O)_2Cbi(III)/Cbi(II)$ | 0.51 | |

Removal of the β-Axial Ligand of Cobalamins

Figure 2:
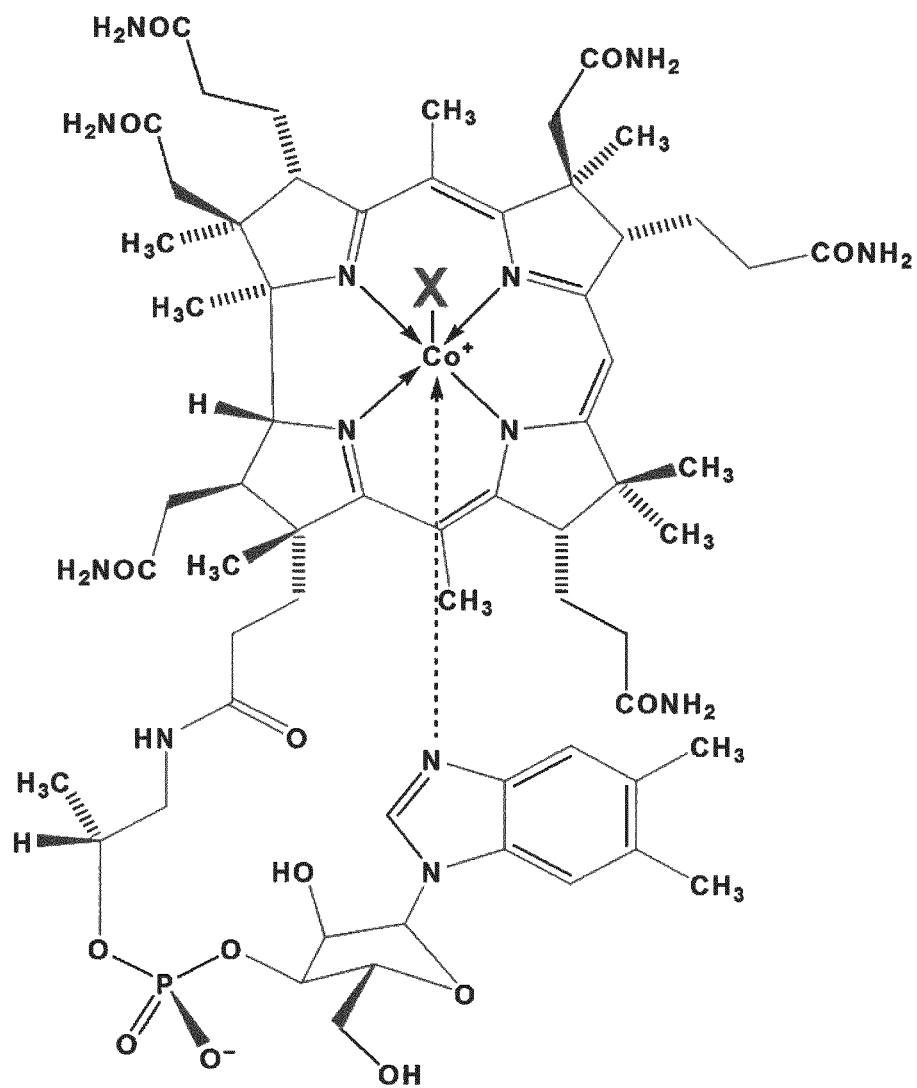
FIG. 2 shows the structure of cobalamins.

Break up of the p-axial ligand of dietary cobalamins (marked as 'X' in FIG. 2) is an indispensable step for the utilization of the micronutrient by humans. This step is catalyzed by the enzyme CblC. Cobalamins are tetrapyrroles assembled in a corrin macrocycle with cobalt as the metal center. Cobalamins possess seven side chains, namely, acetamides and propionamides. The fifth axial coordinating position (α-ligand) is occupied by a nitrogen atom from the dimethylbenzimidazole moiety. The sixth coordination position (herein shown as 'X'), known as the β-ligand, can be occupied by different types of ligands. Naturally occurring ligands include methyl (methylcobalamin), 5-deoxyadenosine (adenosylcobalamin), hydroxo or aqua (hydroxocobalamin, aquacobalamin), cyano (cyanocobalamin), glutathionyl (glutathionylcobalamin) and so forth.

New ligands as disclosed herein will be attached to position X, such to preserve the structure of the cobalamin for optimal binding and transport by transcobalamin. With the exception of small exchangeable ligands such as for example sulfite, nitrite and imidazole, Co—S and Co—C bonded cobalamins require enzymatic processing inside the cells, in order to become bioactive and suitable to fulfill the enzymatic reactions of recipient enzymes methionine synthase (MS) and methylmalonyl-CoA mutase (MCM). The CblC proteins plays an essential role in the intracellular processing of all dietary cobalamins: CblC generates the base-off configuration of cobalamins, which in turn raises the redox potential for the reduction of the cobalt center, thereby facilitating elimination of the p-axial ligand by trans-weakening effect (mediated by the base-off configuration) and facile reductive elimination (mediated by an increased redox potential). In patients with a mutated CblC protein, these thermodynamically and kinetically uphill reactions are blocked, leading to failures in cobalamin processing that lead to elevated homocysteine and methylmalonic acid, the substrates of the two $B_{12}$-dependent enzymes, MS and MCM. The new sulfur-containing cobalamin derivatives described in this invention are chemically "primed" for self-reliant bioactivity, thereby bypassing the crucial protein CblC.

The cobalamin derivatives described herein have a self-reliant, increased bioactivity.

The new generation of vitamin $B_{12}$ derivatives described herein present properties that are favorable not only to treat patients with the cblC disorder, but also, to treat or supplement individuals with other genetic disorders of vitamin $B_{12}$, such as cblA, cblB, cblD, cblF, cblJ, cblX, mut, cblG. This includes intrauterine treatment of embryos and fetuses of mothers who carry a mutation in any of genes involved in vitamin $B_{12}$ metabolism, as a preventative measure during embryogenesis and early development. The new bioactive cobalamins can also be adopted to supplement or treat the elderly (suffering from natural, age-related poor absorption of vitamin $B_{12}$), patients with neurological diseases suffering from age- or dietary-related poor availability of vitamin $B_{12}$, and vegetarians and vegans whose dietary intake of the micronutrient may be lower than required for optimal health. Further, the positive effects of certain thiolatocobalamins on cell survival under conditions of oxidative stress suggest that in addition to the specific roles described in this invention, the newly designed compounds shall bear additional physiological advantages.

Example 1: Ligands Featuring Co—S Bond Formation (Thiolatocobalamins). Synthesis of Thiolatocobalamin Derivatives New thiolatocobalamins were synthesized from the reaction of aquacobalamin (or hydroxocobalamin, both being cob(III)alamin) with 1.3 to 1.9 equivalents of the respective ligands in an analogous manner, as described for other thiolatocobalamins.

Hydroxycobalamin hydrochloride which is commercially available was provided as aqueous solution (typically 10-15%). The hydroxycobalamin hydrochloride solution was reacted with the ligand whereby all syntheses were carried out under red-light-only conditions due to the light sensitivity of the thiolatocobalamins.

Figure 3:
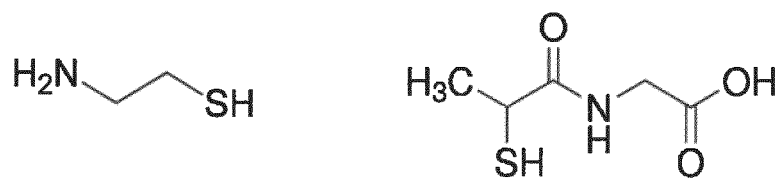
FIG. 3 shows two exemplary ligands, cysteamine and mercaptopropionylglycine with the structure of Cysteamine (left) and Mercaptopropionylglycine (right).

FIG. 3 shows two exemplary ligands, cysteamine and mercaptopropionylglycine with the structure of Cysteamine (left) and Mercaptopropionylglycine (right). Cysteamine is a commercially available aminothiol utilized to treat cystinosis. Mercaptopropionylglycine is available commercially. These aminothiols react with aquocobalamin via a ligand substitution reaction to form the corresponding thiolatocobalamins.

The reactions were performed at room temperature or on ice, under normal conditions, protected from light. The thiolatocobalamins were isolated by precipitation with cold acetone (−20° C.) followed by washing with cold acetone, vacuum filtration and drying overnight at 60° C. The purity of the Cbl products was determined by $^1$H-NMR, mass spectrometry and by conversion to dicyanocobalamin using standard procedures in the art. Newly synthesized Cbl derivatives were further purified using HPLC. Samples were protected from light at all times as the Co—S bond is photolabile.

Figure 4:
FIG. 4 shows the structure of Chloro-methylsulfanyl-methane (left) and 1-Chloro-2-methylsulfanyl-ethane (right).

Example 2: Ligands Featuring Co—C Bond Formation (Alkylcobalamins). Synthesis of Methyl-Sulfide Containing Methylcobalamin Analogues Chloromethyl methyl sulfide and chloroethyl methyl sulfide as shown in FIG. 4 were reacted anaerobically, under dim-red light, with cob(I)alamin pre-reduced with sodium borohydride as described for other alkylcobalamins. two halogenated sulfur containing hydrocarbons react with the supernucleophile cob(I)alamin to produce the corresponding alkylcobalamin derivatives. The halogen serves as the leaving group in these reactions. An excess of the ligand was added and the reaction mixture was allowed to react for 10 minutes at room temperature. The Cbl products were precipitated with cold-acetone, washed and dried overnight at 60° C. Purity of the Cbl products was determined by ¹H-NMR, mass spectrometry and by conversion to dicyanocobalamin using standard procedures. When the purity was lower than 95%, the newly synthesized Cbl derivatives were purified using HPLC. Samples were protected from light at all times.

Example 3: UV-Visible Spectroscopy

The UV-visible spectra of newly synthesized cobalamin derivatives was determined in EPPS buffer (40 mM, pH 7.6, I=1.0 M with sodium triflate). The reaction of aquacobalamin with cysteamine and mercaptopropionylglycine was monitored by time-resolved spectral scanning of reactions containing a fixed amount of aquacobalamin (10-25 μM (micromolar)) and various concentrations of the ligand.

Mercaptopropionylglycine reacted readily with aquacobalamin to form a stable MPGCbl complex at pH 7.2. The observed reaction rate ($k_{obs}$) exhibited a linear dependence with the concentration of ligand, mercaptopropionylglycine.

Figure 5:
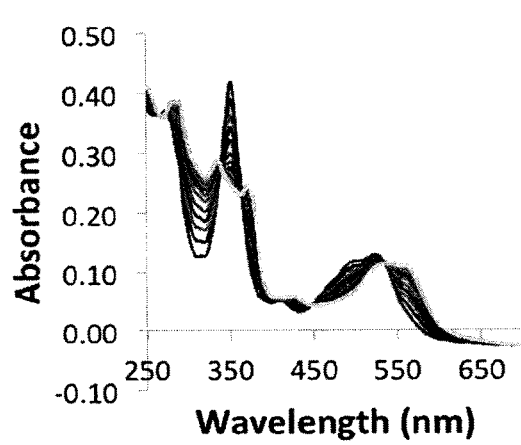
FIGS. 5a, 5b, and 5c depict the results of the reaction between a fixed concentration of aquacobalamin with varying concentrations of the ligand MPG.
Figure 5:
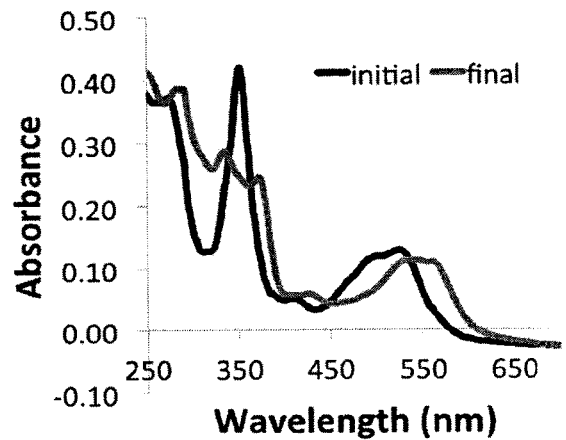
Figure 5:
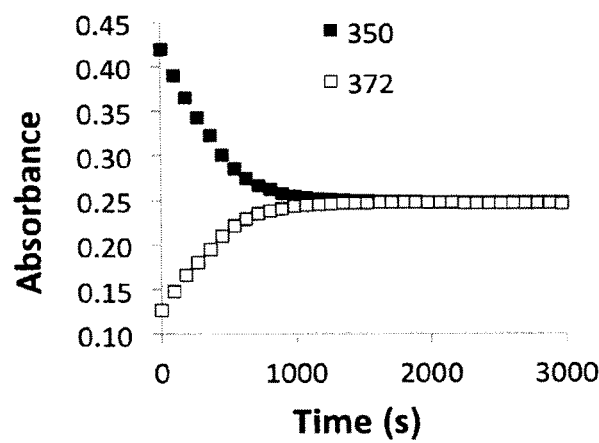

A fixed concentration of aquacobalamin was reacted with varying concentrations of the ligand MPG. The reaction was monitored by time-resolved UV-visible spectroscopy for a total of 50 minutes (FIG. 5). The spectral changes were consistent with the conversion of aquacobalamin into MPGCbl (FIG. 5 a) via a mechanism that involves no detectable reaction intermediates. Initial and final spectra are analyzed to confirm the identity of the thiolatocobalamin product (FIG. 5 b). Time courses were generated at the absorption maxima of each species (350 nm, $H_2OCbl^+$, and 372 nm, MPGCbl) (FIG. 5 c).

Figure 6:
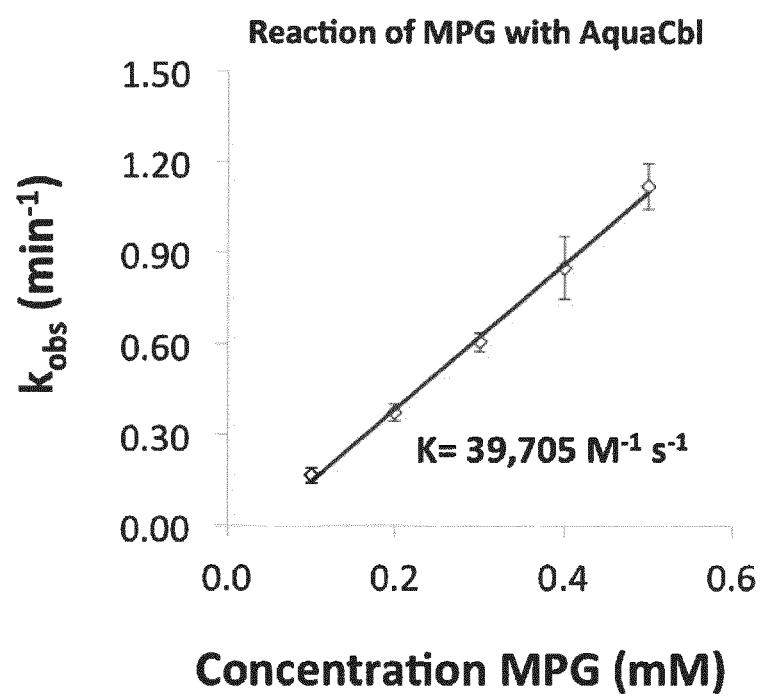
FIG. 6 shows the dependence of the observed reaction rate (kobs) with the concentration of mercaptopropionylglycine ligand for the formation of MPGCbl, in buffer EPPS (40 mM, pH 7.2, I=1.0 M).
Figure 7:
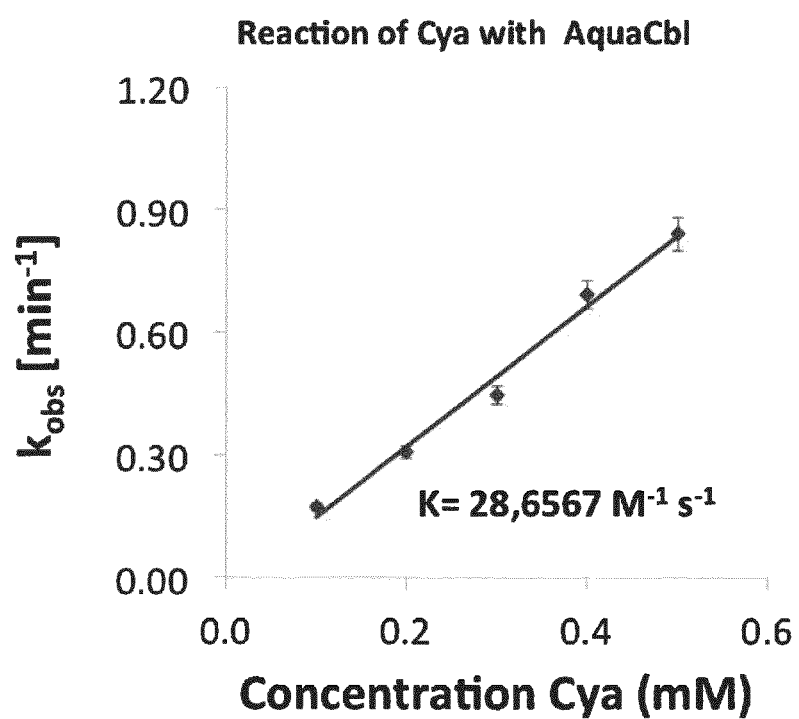
FIG. 7 shows the dependence of the observed reaction rate (kobs) with varying concentrations of cysteamine ligand for the formation of CyaCbl, in buffer EPPS (40 mM, pH 7.2, I=1.0 M).

As demonstrated by FIGS. 6 and 7, cysteamine reacted readily with aquacobalamin to form a stable complex at pH 7.2. The observed reaction rate (kobs) exhibited a linear dependence with the concentration of ligand, cysteamine.

Importantly, the concentration-dependent reaction rates of the new Cbl derivatives are in good agreement with those reported for other thiolatocobalamins.

| Cobalamin | K [$M^{-1}s^{-1}$] | Conditions |
|---|---|---|
| MPGCbl | 39.71 | pH 7.2, l = 1, sodium triflate |
| CyaCbl | 28.66 | pH 7.2, l = 1, sodium triflate |
| GSCbl | 20.74 | pH 7.2, l = 1, sodium triflate |
| GSCbl | 18.09 | pH 7.72, l = 0.5, $KNO_3$ |
| CaptoprilCbl | 24.7 | pH 7.72, l = 0.5, $KNO_3$ |

Example 4: pKa Base-on/-Base-Off Configuration of the New Cbl Derivatives

Cobalamins transitioning from the base-on to the base-off configuration undergo a marked shift of their UV-visible spectra, which was exploited to determine the pKa for this transition. UV-visible spectra of cobalamin derivatives were recorded at different pHs, using a universal buffer mixture. For Co—S bonded cobalamins, the pKa of the base-on to base-off transition was determined by stopped-flow, using human CblC protein as the agent causing the transition, at various pHs, within the physiological range. Thiolatocobalamins undergo proton-catalyzed decomposition (with loss of the thiolate ligand), and therefore, their pKa cannot be determined using standard techniques.

Figure 8:
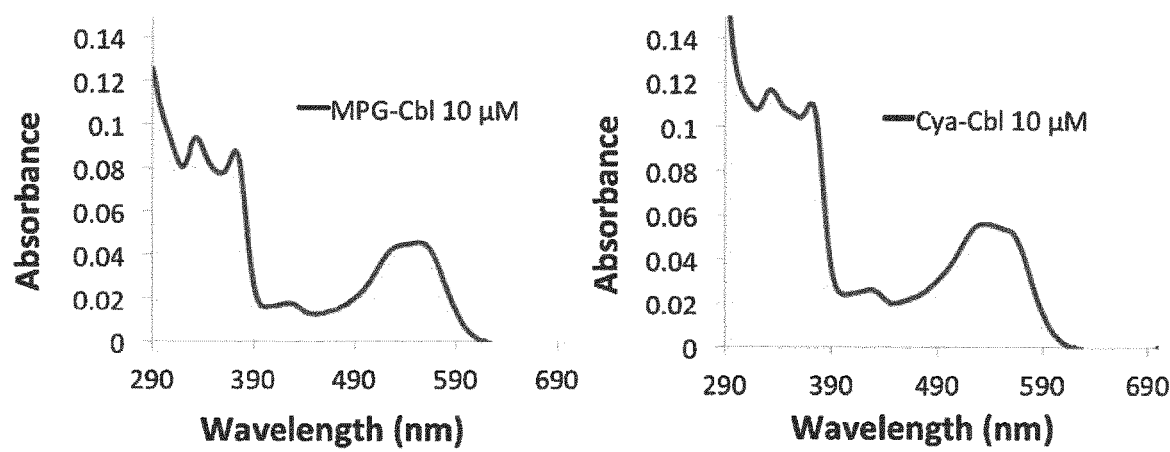
FIG. 8 shows UV-visible spectra of MPGCbl (left) and CyaCbl (right) in 40 mM EPPS, pH 7.6. The absorption maxima of each cobalamin are in agreement with those of previously published thiolatocobalamins.

UV-visible spectra are shown in FIG. 8. The newly synthesized thiolatocobalamins exhibit spectral properties identical to that of previously synthesized Co—S ligated species.

Absorption maxima for CyaCbl and MPGCbl appear at 370 nm and 531 nm, in accord with the properties of previously described Co—S cobalamins.

Absorption coefficients are shown in Table 4. The molar extinction coefficients were also determined using spectrophotometrical methods. The values are described in Table 4. GSCbl was utilized as positive control representing a known and well-characterized thiolatocobalamin.

TABLE 4

Absorption coefficients of CyaCbl, MPGCbl and GSCbl using water as solvent. The table shows the major absorption bands and the error associated to each measurement.

| | Wavelength (nm) | Absorption coefficient (mean ± standard deviation) $M^{-1}cm^{-1}$ | % Error |
|---|---|---|---|
| CyaCbl | 370 | 11166 ± 569 | 5.1 |
| | 531 | 6000 ± 458 | 7.6 |
| MPGCbl | 372 | 10433 ± 651 | 6.2 |
| | 532 | 5133 ± 351 | 6.8 |
| GSCbl | 372 | 11600 ± 200 | 1.7 |
| | 533 | 6200 ± 100 | 1.6 |

Example 5: Determination of the Midpoint (Redox) Potential of Cobalamins

The midpoint potential of the newly synthesized Cbls was determined using spectrochemical and electrochemical techniques. The redox potential of MeCbl and CNCbl, compared with well-studied cobalamins was used as a standard for these measurements.

Example 6: Crystallization of Co—C and Co—S Derivatives

To elucidate the molecular structure of the new Cbl derivatives, crystals were obtained suitable for x-ray crystallographic analysis. Cbl derivatives (50-100 mg/mL) were set in acetone-vapor diffusion vials using various pH, salts and temperatures, as reported in the literature.

Figure 9:
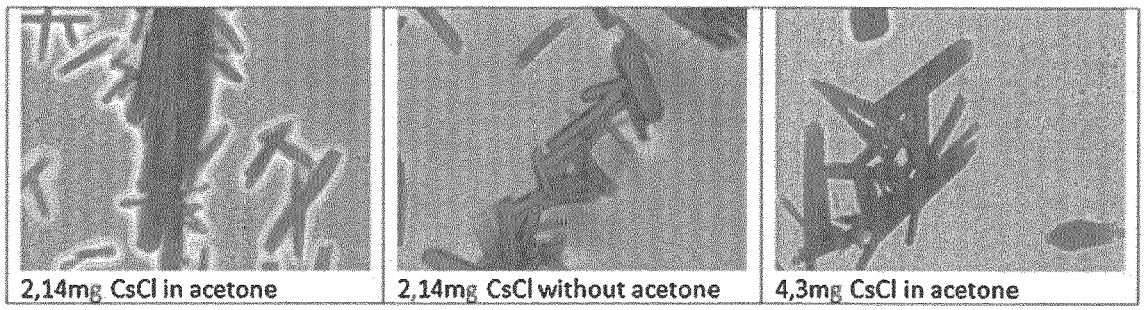
FIG. 9 shows crystals of CyaCbl and MPGCbl grown under various experimental conditions. The original crystals are red in color.
Figure 9:
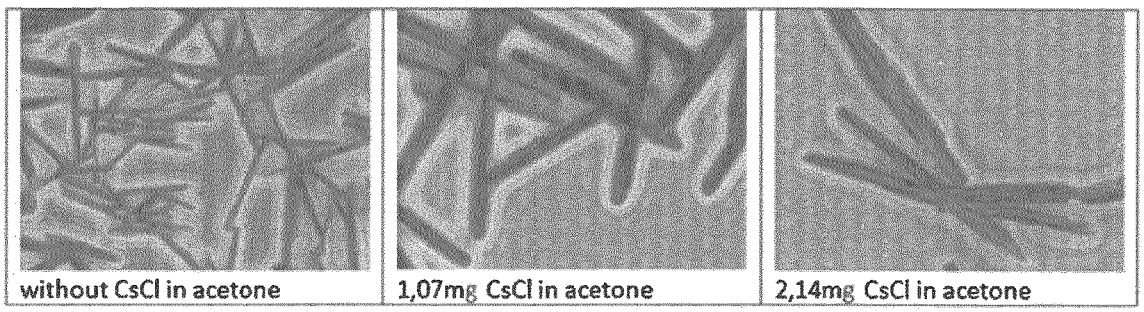

Crystals of CyaCbl and MPGCbl were grown successfully via vapor-diffusion in acetone, at 4° C., in the dark (FIG. 9). Addition of CsCbl favored formation of crystals with size suitable for x-ray analysis. Crystals of CyaCbl formed both with and without acetone vapor diffusion; however, crystals of MPGCbl only grew under acetone vapor diffusion. The ability to isolate the compounds of this invention in crystal-pure form constitutes an advantage for further therapeutic development. Mass spectrometry analysis confirmed the appropriate molecular mass, as follows: [M/2+1], m/z=765 for MPGCbl and m/z=722 for CyaCbl.

Example 7: Stability of the β-Axial Ligand of Co—C and Co—S Derivatives in the Presence of Biologically Relevant Low-Molecular Weight Thiols The stability of newly synthesized Cbl derivatives in the presence of excess GSH, Cys and Hcy was examined by time-resolved UV-visible spectroscopy. Relevant concentration of these cellular thiols was utilized, such as for example, 1-10 mM GSH (reduced glutathione).

The reactivity of newly designed compounds, being Co—S or Co—C ligated with the major intracellular low molecular weight thiol glutathione, was investigated spectrophotometrically. No reaction was observed at pH 7.4 and under aerobic conditions, suggesting that the newly synthesized cobalamins are stable under near physiological conditions.

Example 8: Reactivity with Biologically Relevant Protein Reductases

The reactivity of the new Cbl derivatives toward non-dedicated cellular reductases was evaluated spectrophotometrically. Briefly, the new cobalamins were incubated anaerobically with novel reductase 1 (NR1), methionine synthase reductase (MSR) and flavodoxin reductase (FLDR) and the appropriate cofactors (NADPH, NADH, FAD, etc.).

Conversion of Co—S or Co—C bonded cobalamins to cob(II)alamin or cob(I)alamin was detected by formation of absorption bands at 450 and 467 nm, respectively.

Example 9: Binding of the New Cobalamin Derivatives to Transcobalamin (TC) and to CblC Because cellular uptake of vitamin $B_{12}$ requires binding to transcobalamin and recognition of the TC-$B_{12}$ complex by the transcobalamin receptor CD320, it was determined whether the synthetic Cbl derivatives bind to bovine recombinant and human TC. Binding assays and affinity measurements were carried out using UV-visible spectroscopy and gel filtration. Fractions containing TC were collected, and the presence of bound cobalamin was determined spectrophotometrically. All cobalamins tested so far bind to TC in a stable fashion, and the corresponding TC•Cbl complexes are taken up by cultured cells at comparable rates and yields as seen in current therapeutic forms, HOCbl and CNCbl.

Figure 10:
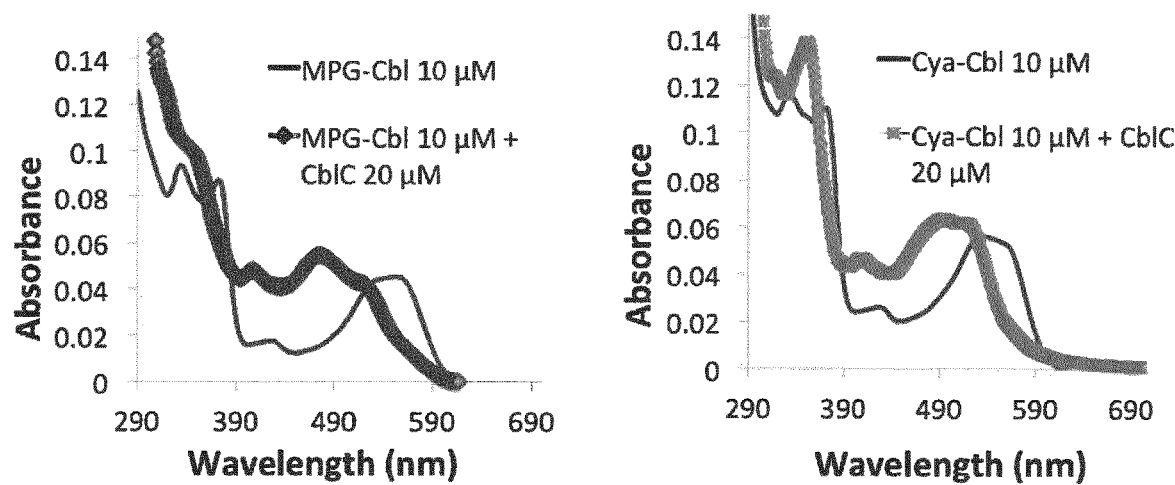
FIG. 10 depicts the binding of CyaCbl (right) and MPGCbl (left) to human wild type CblC at pH 7.0. Binding of base-on CyaCbl or MPGCbl (thin black traces) to CblC induces their respective base-off configuration (thick traces).

An important aspect for the bioactivity of the new compounds is their ability to bind to the processing enzyme CblC, and to undergo conversion to the base-off configuration, which enhances their reactivity. This is a critical step in all intracellular pathways of vitamin $B_{12}$ metabolism that are involved in pathogenesis, and certainly, relevant to the cblC disease itself. For example, mutant variants of the cblC protein known to be pathogenic in humans could be rescued with new bioactive cobalamins, if their intrinsic chemistry is superior to that of the dietary isoforms MeCbl, AdoCbl and HOCbl. Binding studies were conducted at pH 7.6 (EPPS buffer, 0.04 M) and analyzed by UV-visible spectrophotometry. As can be seen from FIG. 10, binding of CyaCbl or MPGCbl to human wild type CblC induces their base-off configuration. This demonstrates that the selected β-ligands do not disrupt the ability of the protein to stably bind to the new cobalamin.

Example 10: Binding of the New Cobalamin Derivatives to Wild Type and Mutant Variants of the CblC Protein Binding of the new Cbl derivatives to wild type and mutant CblC were examined by UV-visible spectroscopy as described for the naturally occurring Cbl isoforms. Binding affinities were determined by isothermal titration calorimetry (ITC, Microcal) or microscale thermophoresis (MST, Nanotemper).

Figure 11:
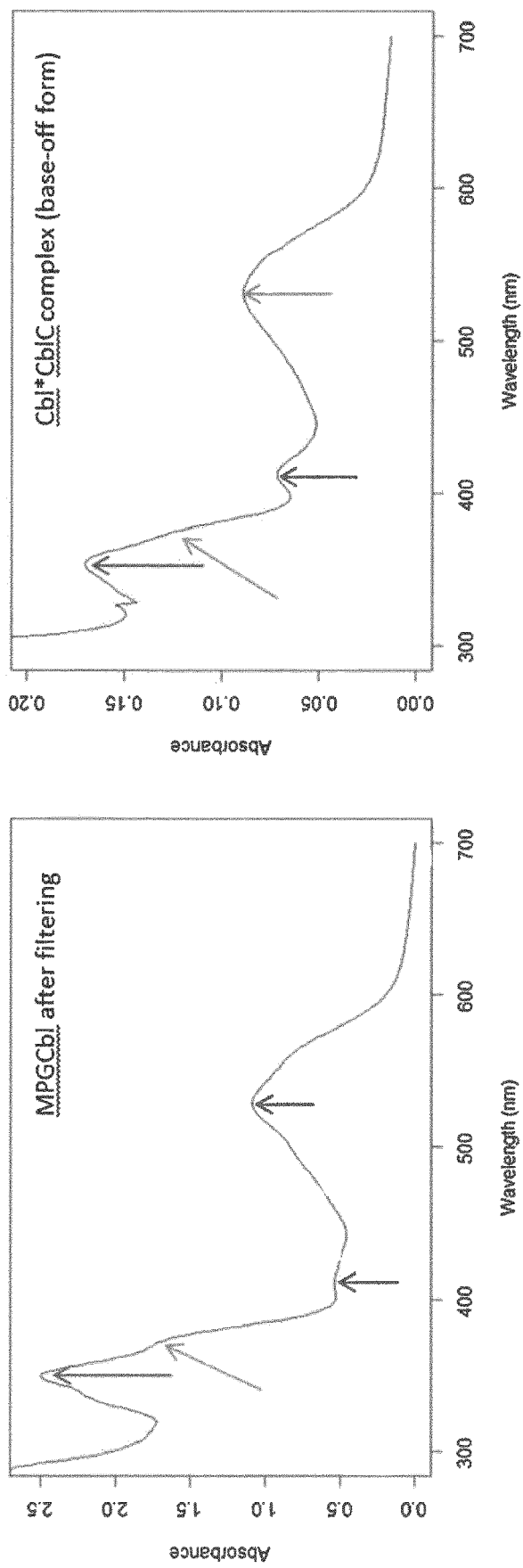
FIG. 11 depicts the spectral similarities between freshly purified MPGCbl dissolved in water, and the base-off configuration of MPGCbl bound to human recombinant CblC protein.

UV-visible spectral analysis of the MPGCbl product after acetone precipitation and vacuum filtration suggested that at least a fraction of this Cbl derivative may exist in its base-off configuration, even in the absence of the CblC protein (FIG. 11). The left panel of the figure shows the UV-visible spectrum of MPGCbl in water, after acetone precipitation and vacuum filtration. The panel on the right shows the authentic base-off spectrum of MPGCbl, when it is bound to the CblC protein. This indicates that MPGCbl may be self-sufficient for its base-on to base-off transition, due to axial ligand electron-donating effects, in the absence of the CblC protein. This finding is particularly relevant to patients with total deletions of the CblC gene, thus exhibiting the most severe phenotype of the cblC disease.

Example 11: CblC Activity Assay

Figure 12:
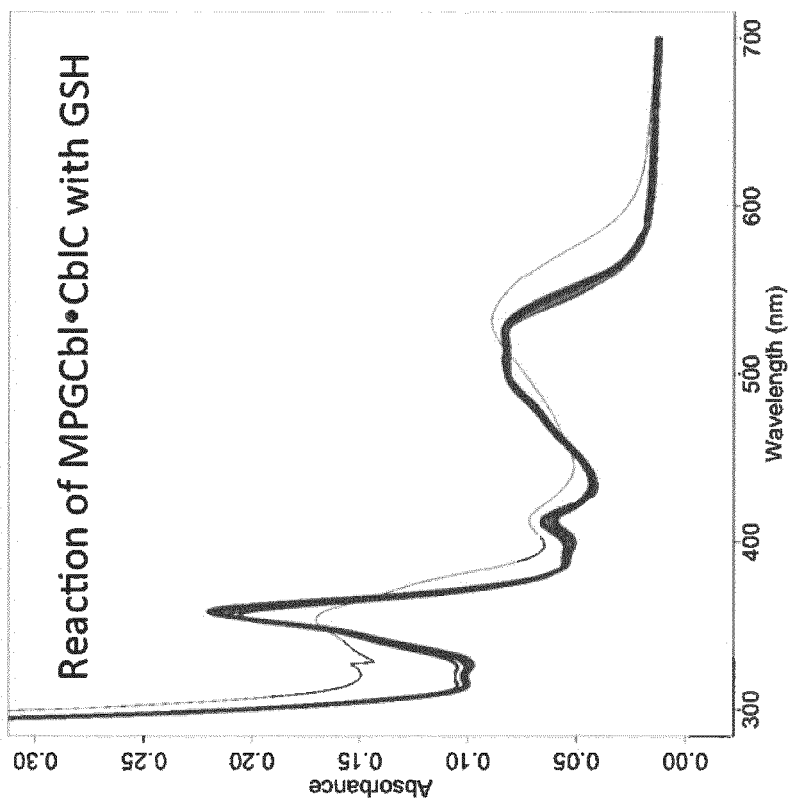
FIG. 12 shows the evaluation of the bioactivity of CyaCbl and MPGCbl in supporting the enzymatic reaction of human recombinant CblC.
Figure 12:
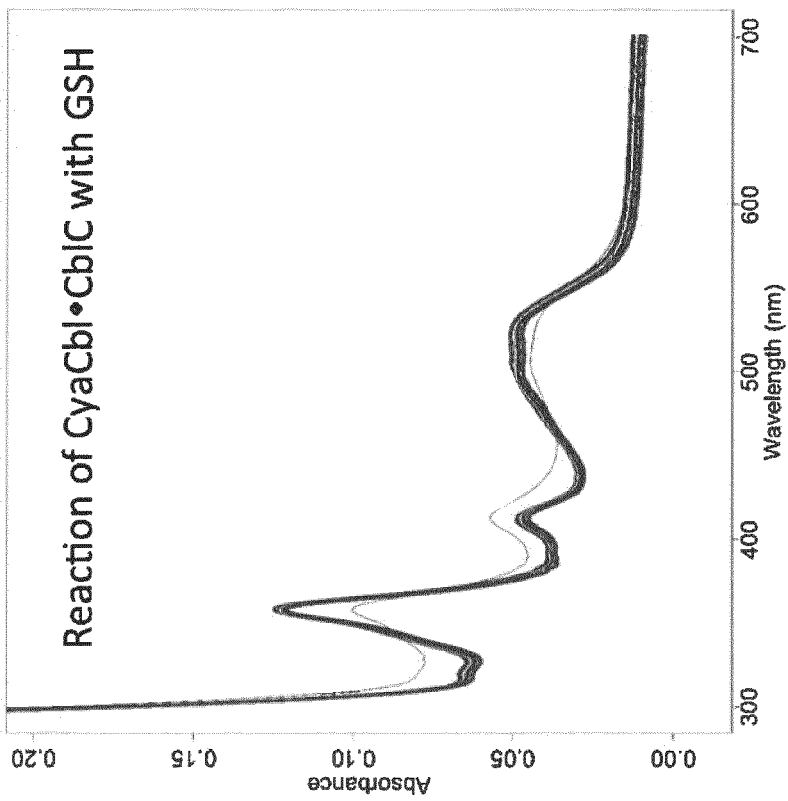

The ability of the newly synthesized Cbl derivatives to serve as substrates for CblC was examined (FIG. 12). CblC activity was measured by UV-visible spectroscopy according to published procedures. Analysis of reaction products was performed by mass spectrometry. We measured dealkylation and de-thiolation of Co—C and Co—S bonded Cbl derivatives, respectively, by wild type and mutant CblC proteins to determine whether these reactions could be supported in patients harboring an abnormal isoform of CblC with low or no enzymatic activity.

FIG. 12. Spectral changes associated to the reaction of CyaCbl or MPGCbl bound to human CblC, in the presence of GSH. The reactions were complete in less than 10 seconds. The initial spectrum is shown as light grey traces. The product of the reactions in both cases is $H_2OCbl^+$ bound to the human CblC protein.

Example 12: Cellular Characterization of Candidate Pro-Drugs

Cbl derivatives exhibiting promising biochemical activity were examined in our collection of cultured control and cblC mutant human fibroblasts. Cultured cells from control (healthy neonatal subjects) or cblC fibroblasts were supplemented without exogenous Cbl (negative control), with commercial CNCbl (current therapy control) or with the newly synthesized cobalamins (test group). The ability of these compounds to support intracellular Cbl metabolism in the absence of CblC was examined by monitoring disease biomarker metabolites Hcy and MMA levels in the conditioned medium.

The enzymatic activity of CblC in the presence of CyaCbl and MPGCbl as substrates was evaluated under the same experimental conditions utilized to examine dealkylation of MeCbl and AdoCbl. Notably, dethiolation of CyaCbl and MPGCbl occurs orders of magnitude faster than in those with MeCbl and AdoCbl. The reaction was complete in less than 10 seconds, which is the time it takes to record the first spectrum after mixing of CblC-bound to CyaCbl or MPGCbl with 5 mM GSH (FIG. 12). These results indicate that the new cobalamin derivatives have markedly increased bioactivity in terms of enzymatic processing by the CblC protein.

Example 13: Restoral of Intracellular Cobalamin Metabolism Using Radioactive Derivatives of the New Drugs ($^{57}$Co)-containing species are synthesized to be used as a Cbl source for intracellular Cbl profiling, i.e. conversion of new ($^{57}$Co)-thiolato- or ($^{57}$Co)-sulfur-containing alkylcobalamins to $^{57}$Co-AdoCbl and $^{57}$Co-MeCbl as it was described in a previous publication of Hannibal et al. (Mol. Genet.Metab. (2009) p. 260).

Example 14: Examination of the cblC Proteome after Treatment with New Co—S or Co—C Cobalamins, Compared to Studies Using Hydroxocobalamin Available in the Art Previous proteomic studies in the literature showed that the proteome of skin fibroblasts isolated from patients with cblC disease responded poorly to treatment with CNCbl or HOCbl, the current therapeutic forms. A global proteomic study using SILAC (Stable Isotope Labeling of Amino Acids in Cell Culture) was carried out to compare the ability of current therapies (hydroxocobalamin/cyanocobalamin) versus new drug candidates in restoring the cblC cellular proteome to the expression patterns of cells isolated from healthy neonatal subjects. Reversal of the cblC phenotype (or that of other metabolic diseases involving abnormalities of cobalamin trafficking or processing) to that of healthy subjects is utilized as a measure of therapeutic success ex vivo.

Example 15: Assessment of the Biological Activity of CyaCbl, MPGCbl and Me-S-MeCbl with Respect to Previously Described Thiolatocobalamin GSCbl (Model of Co—S), and the Natural Cofactor Methylcobalamin (Model of Co—C)

First, the ability of novel cobalamins described herein was tested to act as substrate for wild type CblC and to restore the lost activity of pathogenic variants, such as mutant Arg161Gly, that leads to early-onset form of the cblC disease. Table 5 shows the results of enzymatic activity measurements with human recombinant CblC wild type and pathogenic mutant Arg161Gly.

product. Stabilization of cob(II)alamin by the mutant Arg161Gly in the presence of MeCbl and high concentration of GSH has been described earlier. Herein, a similar mechanism is identified but with increased bioactivity, i.e. with reaction half-lives comparable to those of wild type CblC.

Second, results from the analysis of thiolatocobalamins showed that a previously reported thiolatocobalamin, GSCbl, is able to support the reaction of CblC, wild type and pathogenic variant Arg161Gly, albeit 4-5-fold less proficiently than the two of the thiolatocobalamin derivatives described in this invention, namely MPGCbl and CyaCbl.

Figure 13:
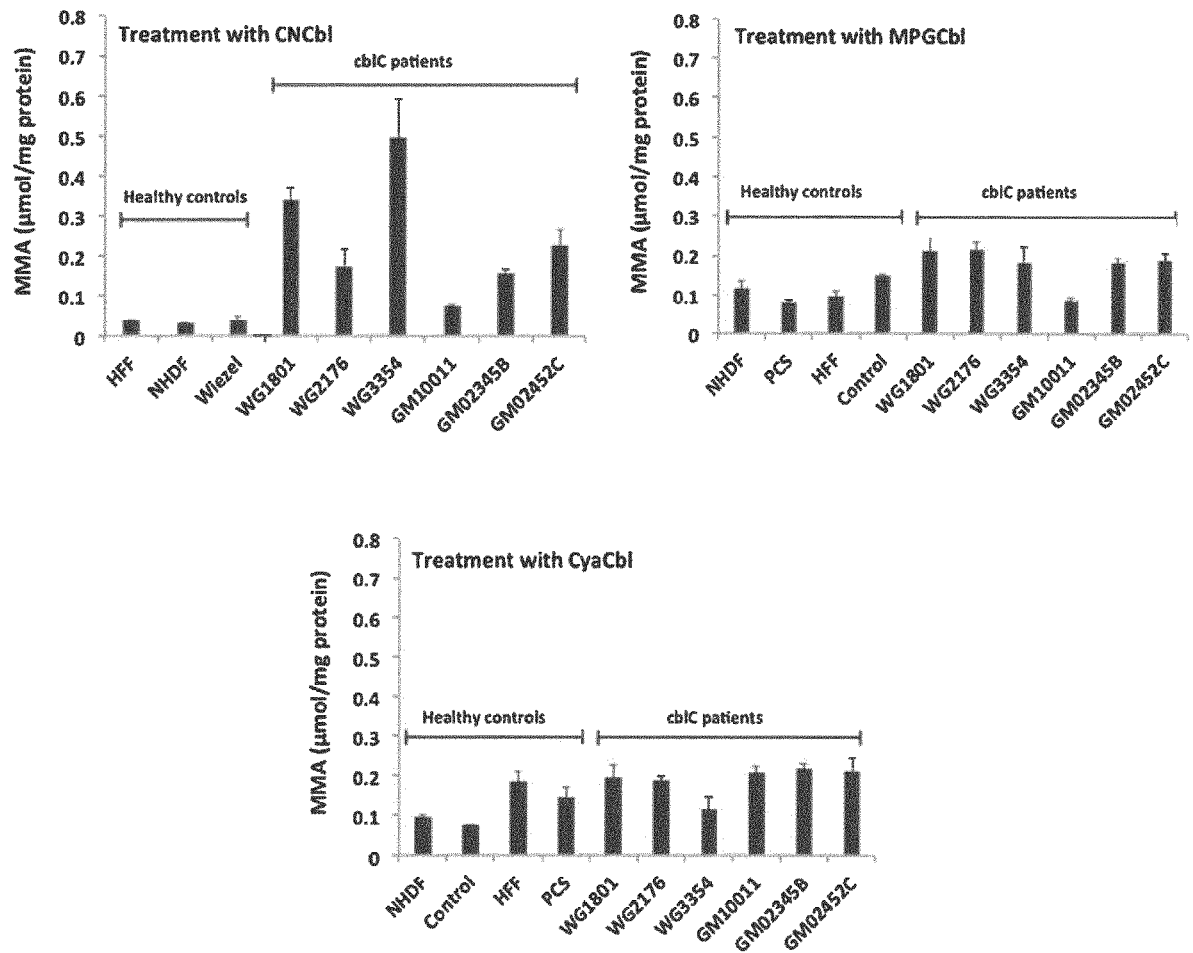
FIG. 13 provides a comparison of the effect of CNCbl (0.001 mM) versus the same dose of CyaCbl or MPGCbl given to cultured fibroblasts from healthy subjects (HFF, NHDF, PCS, Wiesel, Control) or from cblC patients (WG1801, WG2176, WG3354, GM10011, GM02345B, GM02452C).

Example 16: Assessment of the Biological Activity of CyaCbl and MPGCbl in Human Cultured Cells Isolated from Healthy Subjects or from cblC Patients: Analysis of Methylmalonic Acid, a Biomarker of Cobalamin Deficiency The cellular response to treatment with new derivatives CyaCbl and MPGCbl in comparison with current therapeutic form CNCbl was measured. The ability of the new cobalamin derivatives CyaCbl and MPGCbl to achieve metabolic control, i.e. reduction of for example MMA production by cblC fibroblasts in culture, was examined as described in previously published experimental protocols. FIG. 13 provides a comparison of the effect of CNCbl (0.001 mM) versus the same dose of CyaCbl or MPGCbl given to cultured fibroblasts from healthy subjects (HFF, NHDF, PCS, Wiesel, Control) or from cblC patients (WG1801, WG2176, WG3354, GM10011, GM02345B, GM02452C). As can be seen from these results, CyaCbl and MPGCbl are far superior compared to CNCbl in reducing MMA to the levels observed in fibroblasts from healthy subjects.

TABLE 5

Enzymatic activity of CblC, wild type and pathogenic mutant Arg161Gly in the presence of novel sulfur-containing cobalamins in reactions driven by glutathione (GSH).

| Cobalamin | Half-life of beta-axial ligand removal (minutes)* | | Product under ambient conditions | |
|---|---|---|---|---|
| | Wild type CblC | Mutant Arg161Gly | Wild type CblC | Mutant Arg161Gly |
| MeCbl | 10 | 60 | $H_2OCbl$ | Cob(II)alamin |
| PrCbl | 318 | 0 | $H_2OCbl$ | No reaction |
| BuCbl | 1155 | 0 | $H_2OCbl$ | No reaction |
| Me—S—MeCbl | 8.5 | 12 | $H_2OCbl$/Cob(II)alamin | Cob(II)alamin |
| Me—S—EtCbl | 7.5 | 11.5 | $H_2OCbl$/Cob(II)alamin | Cob(II)alamin |
| GSCbl | 2.5 | 9.8 | $H_2OCbl$ | $H_2OCbl$ |
| MPGCbl | <0.5 | 1.5 | $H_2OCbl$ | $H_2OCbl$ |
| CyaCbl | <0.5 | 2.1 | $H_2OCbl$ | $H_2OCbl$ |

Abbreviations:
PrCbl: propylcobalamin (structural analogue for Me—S—MeCbl);
BuCbl: butylcobalamin (structural analogue for Me—S—Et—Cbl);
GSCbl: glutathionylcobalamin (analogue for thiolatocobalamins)
*Dealkylation of Co-C cobalamins was carried out with CblC-alkylCbl complexes (20 μM:10 μM) in EPPS buffer (40 mM, pH 7.6) supplemented with 150 mM NaCl and 10% glycerol at 25° C. The reactions were started by addition of 5 mM GSH and monitored for 60 minutes.
Dethiolation of Co—S cobalamins was carried out with CblC-alkylCbl complexes (20 μM:10 μM) in EPPS buffer (40 mM, pH 7.6) supplemented with 150 mM NaCl and 10% glycerol at 25° C. The reactions were started by addition of 50 μM GSH and monitored for 60 minutes. The reactions were monitored by UV-visible spectrophotometry (one full scan (300 to 700 nm) was collected every 2 minutes).

First, the data show that the sulfur-containing alkylcobalamins Me-S-MeCbl and Me-S-EtCbl are superior compared to the natural cofactor MeCbl and to their corresponding sulfur-lacking analogues propylcobalamin and butylcobalamin. In fact, PrCbl and BuCbl are unable to restore the enzymatic activity of pathogenic CblC variant Arg161Gly, whereas the two novel cobalamins described in this invention can support this reaction, to yield cob(II)alamin as the Additional examination of the effect of thiolatocobalamins CyaCbl and MPGCbl and sulfur-containing alkylcobalamin Me-S-MeCbl with respect to structural analogues that are NOT available for therapy was also carried out, for comparative purposes. The results of cellular response (healthy controls and cblC patient fibroblasts) to cobalamin treatment, as reflected by MMA levels is provided in Table 6.

TABLE 6 shows results obtained with different cell lines partially obtained from patients with cblC disease.

| Subject | MMA (μmol/mg protein) | | | | |
|---|---|---|---|---|---|
| | MeCbl | Me—S—MeCbl | GSCbl | MPGCbl | CyaCbl |
| Concentration of MMA in conditioned medium after 7 days: | | | | | |
| HFF | 0.106 | 0.132 | 0.105 | 0.116 | 0.095 |
| NHDF | 0.152 | 0.103 | 0.078 | 0.096 | 0.184 |
| Wiezel | 0.095 | 0.132 | 0.135 | 0.148 | 0.144 |
| WG1801 | 0.429 | 0.254 | 0.198 | 0.212 | 0.194 |
| WG2176 | 0.459 | 0.083 | 0.316 | 0.216 | 0.189 |
| WG3354 | 0.891 | 0.148 | 0.269 | 0.183 | 0.114 |
| GM10011 | 0.066 | 0.041 | 0.052 | 0.087 | 0.208 |
| GM02345B | 0.250 | 0.150 | 0.223 | 0.182 | 0.217 |
| GM02452C | 0.243 | 0.150 | 0.167 | 0.190 | 0.369 |
| Controls | 0.118 | 0.122 | 0.106 | 0.120 | 0.141 |
| cblC patients | 0.390 | 0.138 | 0.204 | 0.178 | 0.215 |
| Concentration of MMA in conditioned medium after 7 days wash-off period(*) | | | | | |
| Controls | 0.131 | 0.145 | 0.134 | 0.121 | 0.154 |
| cblC patients | 0.298 | 0.177 | 0.275 | 0.185 | 0.190 |

(*)Cells were first cultured in the presence of the given cobalamins for a total period of time of 7 days without replacement of the culture medium. After this, the cultured medium was removed and replaced with fresh medium lacking supplemental cobalamin (wash-off experiment). The cells were grown for another 7 days (wash-off experiment), and the levels of MMA were determined for comparative purposes.
Control healthy fibroblasts used herein are: HFF, NHDF and Wiezel.
Cell lines labeled as WG and GM are fibroblasts isolated from patients with cblC disease.

Altogether, these results show proof of the following events:
(a) CyaCbl and MPGCbl were transported successfully into the cells using the canonical TC transporter and its cellular receptor CD320.
(b) CyaCbl and MPGCbl were not cytotoxic under our experimental conditions.
(c) CyaCbl and MPGCbl could furnish the reaction of mitochondrial MCM to a greater extent than CNCbl, one of the current therapeutic forms.
(d) The fact that mitochondrial metabolism of vitamin $B_{12}$ could be restored by treatment with CyaCbl or MPGCbl suggest that the new derivatives are bioactive both in the cytosol (where Cbl processing occurs) as well as in the mitochondrion, where the micronutrient is essential for the reaction of MCM.
(e) Me-S-MeCbl, MPGCbl and CyaCbl supported enzymatic activity of CblC pathogenic variant Arg161Gly (early onset cblC disease), showing more effective removal of the beta-axial ligands compared to their respective counterparts GSCbl (for thiolatocobalamins) and MeCbl (for Co—C sulfur-containing cobalamins).
(f) Me-S-MeCbl reduced MMA to a greater extent compared to its structural analogue MeCbl, suggesting this sulfur-containing alkylcobalamin exhibits superior activity in restoring intracellular cobalamin metabolism. This sulfur-containing alkylcobalamin reduced MMA accumulation in the culture medium similarly to MPGCbl.
(g) While GSCbl was effective at reducing MMA concentration in cblC fibroblasts, a wash-off experiment showed that the metabolic correction achieved with MPGCbl and CyaCbl lasted longer in time compared to GSCbl, that is, preventing buildup of toxic MMA after cells are devoid of supplemental cobalamin (Table 6). Our data show that MPGCbl and CyaCbl are superior compared to its structural analogue GSCbl in sustaining cobalamin metabolism in cblC fibroblasts over time.

The invention claimed is:

1. A cobalamin derivative of formula (I)

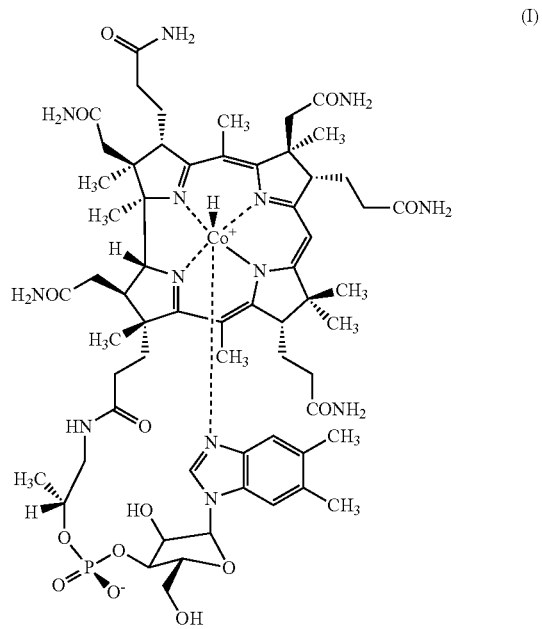

(I)

wherein X is a ligand having the formula:
—$(CH_2)_{1-5}$—S—$(CH_2)_{0-3}$—$CH_3$.

2. The cobalamin according to claim 1 of formula (I), wherein X is selected from the group consisting of:
—$CH_2$—S—$CH_3$, and —$CH_2$—$CH_2$—S—$CH_3$.

3. A pharmaceutical composition comprising a cobalamin derivative according to claim 1 as active pharmaceutical ingredient (API).

4. The pharmaceutical composition according to claim 3 in the form of an orally applicable formulation.

5. The pharmaceutical composition according to claim 3 in the form of a parenterally applicable formulation.

6. A food supplement comprising a cobalamin derivative according to claim 1 and a suitable additive.

7. A method of treating a $B_{12}$-related disease comprising the step of administering to a subject in need thereof the cobalamin derivative according to claim 1.

8. The method according to claim 7, wherein the $B_{12}$-related disease being treated is caused by an impairment of cobalamin complementation group C (CblC).

9. The method according to claim 7, wherein the $B_{12}$-related disease being treated is age-related mental degeneration.

10. The method according to claim 9, wherein the age-related mental degeneration being treated is dementia.

11. The method according to claim 9, wherein the age-related mental degeneration being treated is Alzheimer's disease.

* * * * *